US012006311B2

United States Patent
Roma Castanyer et al.

(10) Patent No.: US 12,006,311 B2
(45) Date of Patent: Jun. 11, 2024

(54) COMPOUNDS FOR USE IN PREVENTING OR TREATING CANCER

(71) Applicants: FUNDACIÓ HOSPITAL UNIVERSITARI VALL D'HEBRON—INSTITUT DE RECERCA, Barcelona (ES); INSTITUT UNIV. DE CIÈNCIA I TECNOLOGIA, S. A., Mollet del Valles (ES)

(72) Inventors: Josep Roma Castanyer, Barcelona (ES); Marta Pascual Gilabert, Barcelona (ES); José Sánchez De Toledo Codina, Barcelona (ES); Soledad Gallego Melcón, Barcelona (ES); Patricia Zarzosa Martínez, Barcelona (ES); Javier Alonso Fernández, Mollet del Valles (ES); Sergio Pérez Ozcáriz, Mollet del Valles (ES); Cristina López Gómez, Mollet del Valles (ES); Josep Castells Boliart, Mollet del Valles (ES)

(73) Assignees: FUNDACIÓ HOSPITAL UNIVERSITARI VALL D'HEBRONINSTITUT DE RECERCA, Barcelona (ES); INSTITUT UNIV. DE CIÈNCIA I TECNOLOGIA, S. A., Mollet del Valles (ES)

( * ) Notice: Subject to any disclaimer, the term of this patent is extended or adjusted under 35 U.S.C. 154(b) by 696 days.

(21) Appl. No.: 17/256,837

(22) PCT Filed: Jul. 1, 2019

(86) PCT No.: PCT/EP2019/067557
§ 371 (c)(1),
(2) Date: Dec. 29, 2020

(87) PCT Pub. No.: WO2020/002701
PCT Pub. Date: Jan. 2, 2020

(65) Prior Publication Data
US 2021/0230150 A1    Jul. 29, 2021

(30) Foreign Application Priority Data
Jun. 29, 2018 (EP) .................................... 18382485

(51) Int. Cl.
C07D 409/14 (2006.01)
A61K 45/06 (2006.01)
A61P 35/04 (2006.01)

(52) U.S. Cl.
CPC ............ *C07D 409/14* (2013.01); *A61K 45/06* (2013.01); *A61P 35/04* (2018.01)

(58) Field of Classification Search
CPC ........ C07D 409/12; A61P 35/04; A61K 45/06
See application file for complete search history.

(56) References Cited

U.S. PATENT DOCUMENTS

| 6,710,058 B2 * | 3/2004 | Jacobson | ............. C07D 409/14 546/205 |
|---|---|---|---|
| 2002/0183324 A1 | 12/2002 | Jacobson et al. | |
| 2004/0006062 A1 | 1/2004 | Smallheer et al. | |

OTHER PUBLICATIONS

Role of nitric oxide in tumor progression: Lessons from experimental tumors, Peeyush K. Lala and Amila Orucevic, 1998, Cancer and Metastasis Reviews 17: 91-106, 1998 (Year: 1998).*

(Continued)

*Primary Examiner* — Noble E Jarrell
*Assistant Examiner* — Richard Grant Peckham
(74) *Attorney, Agent, or Firm* — Leason Ellis LLP

(57) ABSTRACT

The present invention relates to compounds of formula (I) for use in preventing and/or treating cancer.

15 Claims, 3 Drawing Sheets

(56) References Cited

OTHER PUBLICATIONS

Molecular Classiþcation of Cancer: Class Discovery and Class Prediction by Gene Expression Monitoring, T. R. Golub, D. K. Slonim, P. Tamayo, C. Huard, M. Gaasenbeek, J. P. Mesirov, H. Coller, M. L. Loh, J. R. Downing, M. A. Caligiuri, C. D. Bloomfield, 1999, Science vol. 286 Oct. 15, 1999 (Year: 1999).*

The use of common genetic polymorphisms . . . , N. Rothman, S. Wacholder, N.E. Caporaso, M. Garcia-Closas, K. Buetow, J.F. Fraumeni Jr, Aug. 15, 2000, Biochemica et Biophysica Acta 1471 (2001) C1-C10 (Year: 2000).*

Smallheer JM, Wang S, Laws ML, Nakajima S, Hu Z, Han W, Jacobson I, Luettgen JM, Rossi KA, Rendina AR, Knabb RM, Wexler RR, Lam PY, Quan ML. Sulfonamidolactam inhibitors of coagulation factor Xa. Bioorg Med Chem Lett. Apr. 1, 2008;18(7):2428-33. doi: 10.1016/j.bmcl.2008.02.054. Epub Feb. 26, 2008. (Year: 2008).*

Mackman, N. Triggers, targets and treatments for thrombosis. Nature 451, 914-918 (2008). https://doi.org/10.1038/nature06797 (Year: 2008).*

15.12: Thioethers (Sulfides) and Silyl Ethers, p. 1-5, LibreTexts Chemistry, Feb. 2016. https://chem.libretexts.org. (Year: 2016).*

LibreTexts Chemistry: https://a.mtstatic.com/deki/javascript/out/standalone/ui.translateWrapper.js?_=7315bad; p. 1-33; (Year: 2016).*

International Search Report issued in PCT/EP2019/067557, dated Sep. 17, 2019.

Smallheer, Joanne M., et al. "Sulfonamidolactam inhibitors of coagulation factor Xa." Bioorganic & medicinal chemistry letters 18.7 (2008): 2428-2433.

Teglund, Stephan, and Rune Toftgård. "Hedgehog beyond medulloblastoma and basal cell carcinoma." Biochimica et Biophysica Acta (BBA)—Reviews on Cancer 1805.2 (2010): 181-208.

Robinson, Giles W., et al. "Vismodegib exerts targeted efficacy against recurrent sonic hedgehog—subgroup medulloblastoma: results from phase II pediatric brain tumor consortium studies PBTC-025B and PBTC-032." Journal of Clinical Oncology 33.24 (2015): 2646.

* cited by examiner

COMPOUNDS FOR USE IN PREVENTING OR TREATING CANCER

CROSS-REFERENCE TO RELATED PATENT APPLICATIONS

This is a U.S. National Phase Application under 35 U.S.C. § 371 of International Patent Application No. PCT/EP2019/067557, filed Jul. 1, 2019, and claims priority to European Patent Application No. 18382485.3, filed Jun. 29, 2018, which is incorporated by reference in its entirety. The International Application was published on Jan. 2, 2020, as International Publication No. WO2020/002701 A1.

FIELD OF THE INVENTION

The present invention relates to the field of cancer treatment. More in particular, the present invention relates to compounds of formula (I) for use in preventing and/or treating cancer.

BACKGROUND OF THE INVENTION

Hedgehog (HH) pathway-belonging proteins are considered to be key regulators of development in pluricellular organisms, playing crucial roles in processes such as tissue patterning, proliferation and differentiation. Similarly, HH signaling also plays major roles in adult organisms such as stem cell maintenance or tissue repair and regeneration. Beyond its role in healthy tissues, HH signaling has been shown to be deregulated in a very wide range of cancers. The major types (without excluding other cancers not cited) are: basal cell carcinoma, melanoma, medulloblastoma, astrocytoma, lung cancer, prostate cancer, pancreatic cancer, colorectal cancer, breast cancer, ovarian cancer, cervical cancer, glioblastoma, neuroblastoma, digestive tract tumors, leukemia, rhabdomyosarcoma and osteosarcoma, among many others. The pathway has a multifactorial oncogenic role since it may support cell proliferation, tumor progression, metastasis and therapeutic resistance (Teglund et al 2010, Almazán-Moga et al 2017).

The three HH proteins present in mammals, namely Sonic (SHH), Indian (IHH) and Desert (DHH), are ligands of Patched receptors (PTCH1 and PTCH2). Ligand-free PTCH inhibits the activation of Smoothened (SMO) by an incompletely unraveled mechanism. In the absence of active SMO in the membrane, Gli family zinc finger proteins (Gli1, Gli2 and Gli3) in a complex with Suppressor of fused homolog (SUFU) are proteosomically processed. Upon binding of an HH ligand, SMO becomes active and prevents GLI proteosomal processing. GLI is then translocated to the nucleus where it binds to and regulates GLI-specific promoters to activate its specific targets. The three best known direct targets of the pathway are Gli1, Ptch1 and Hhip, genes of the pathway itself (Roma et al., 2012; Manzella et al., 2015).

On the other hand, and more recently, other barely known proteins such as CDO (Cell Adhesion Associated, Oncogene Regulated) and its highly homologous protein BOC (Brother of CDO), which also participate as co-activators of the pathway have been shown to be able to bind to Hedgehog ligands (Okada A 2006, Tenzen T 2006, Allen B L 2007). These co-activators would facilitate activation of the pathway even when very small amounts of ligands are available. In addition, an oncogenic role of these proteins has been described for several adult cancers, with various references involving CDO and BOC in the progression of cancer. To cite the most salient examples: CDO plays a clearly activating role of proliferation and clonogenicity in lung cancer (Leem Y E 2014) and a clear pro-oncogenic role in prostate cancer (Hayashi T 2011). Similarly, a pro-apoptotic role of CDO has been described in neuroblastoma (Gibert B 2014), which suggests that possible inhibition of the interaction between CDO and HH ligands could be a high-potential therapeutic target since it could enable the induction of cell death. On the other hand, BOC is also thought to play a crucial role in the progression and malignisation of medulloblastoma (Mille F 2014).

In this respect, CDO and BOC are unexplored potential putative therapeutic targets, which are overexpressed in rhabdomyosarcoma (RMS) and other cancers. A specific therapy of embryonic components, such as those of the Hedgehog pathway, could have high specificity for tumour cells (since this pathway is prone to being downregulated in normal cells of the body) and, therefore, it has the potential to reduce adverse side effects.

The SMO antagonists, such as Vismodegib, are active in mutation-driven cancers such as basal cell carcinoma and medulloblastoma, but clinical results in other solid tumours whereby mutational activation of the pathway is absent have been less encouraging (McMillan R 2012). For instance, in metastatic pancreatic cancer, a clinical trial with the SMO antagonist Saridegib was prematurely halted after patients were found to have a higher rate of disease progression and lower median survival (McMillan R 2012). More recently, in a randomized Phase Ib/II with Vismodegib in patients with metastatic pancreatic cancer revealed the addition of Vismodegib did not improve overall response rate, event free survival or overall survival (Catenacci DV 2015). Other attempts in metastatic colorectal and ovarian cancer did not render also significant positive results (McMillan R 2012). Moreover, the recent description of a pro-oncogenic off-target effect of Vismodegib may explain its previously reported inefficiency in several ligand-dependent cancers or even the premature halting of some of them owing to survival worsening (Almazen-Moga et al 2017). This raises the possibility of pharmacologic Hedgehog inhibition via the interference of other clue components of the pathway, instead of SMO inhibitors, which may be considered appealing therapeutic alternatives.

In view of the prior art, there is still the need for finding new compounds which are more effective than the known compounds or therapies, while maintaining an acceptable or improved toxicity profile.

Smallheer and colleagues (Smallheer, J. M et al. Sulfonamidolactam inhibitors of coagulation factor Xa. Bioorganic & Medicinal Chemistry Letters 18 (7), 2008, 2428-2433) disclose 3-(sulfonylamino)-2-piperidone compounds as inhibitors of Factor Xa antithrombotic drugs. No reference is made to the use of these compounds for the purposes of the present invention.

US 2004/0006062 discloses sulfonylaminovalerolactams and derivatives thereof useful as inhibitors of trypsin-like serine proteases, specifically factor Xa. These compounds do not include the biphenilic ring system contained in the compounds of the formula (I) of the present invention. No reference is made to the use of these compounds for the purposes of the present invention.

US 2002/0183324 A1 discloses monocyclic or bicyclic carbocycles and heterocycles which are useful as inhibitors of trypsin-like serine proteases, especially factor Xa for the treatment and prevention of thromboembolic disorders. No reference is made to the use of these compounds for the purposes of the present invention.

The present inventors have surprisingly found that compounds of formula (I) exhibit antiproliferative activity in cancer in comparison to known marketed anticancer agents, while at the same time not affecting the normal cell division of certain non tumour cells, i.e. it exhibits no toxic effect on this type of normal cells.

The compounds of formula (I) have demonstrated a very potent anti-cancer activity with an improvement of the response observed when compared to the reference compound (Vismodegib).

SUMMARY OF THE INVENTION

The present invention relates to a compound of formula (I) for use in the prevention or treatment of cancer, alone or combined with a further compound or a further therapy. Said compound can be included in a pharmaceutical composition.

DETAILED DESCRIPTION OF THE INVENTION

Figure 1:
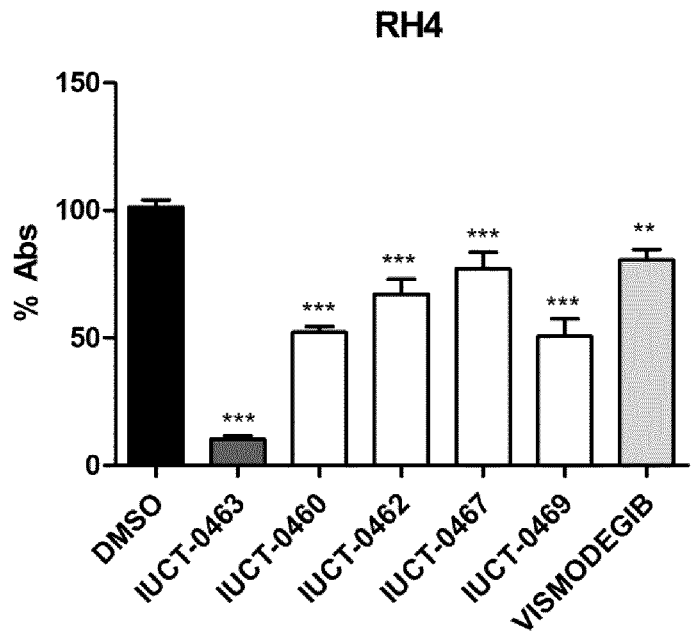
FIG. 1 represents the effects in percentage with respect to vehicle-treated cells (DMSO) of five compounds according to formula (I) (IUCT-0460, IUCT-0462, IUCT-0463, IUCT-0467, IUCT-0469) and the reference compound Vismodegib on cell growth of RH4 rhabdomyosarcoma cells after 5 day incubation (mean+/−SD). All compounds were used at a concentration of 10 microM. Statistical analysis was performed using ANOVA. As statistical differences were observed (p=0), the pairwise comparison against the vehicle control was made using the Tukey test. Notation: *=statistically-significant difference with a p-value<0.001, =p-value<0.01 and *=p-value<0.05.

The present invention relates to a compound having formula (I)

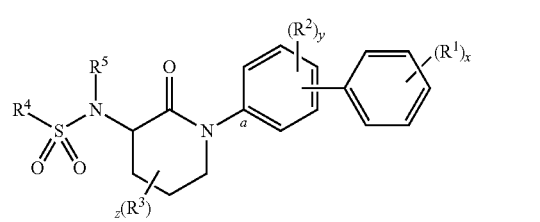

(I)

and the salts and stereoisomers thereof, wherein $R^1$ is hydrogen; OH; $NH_2$; SH; F; Cl; Br; I; methyl; an optionally substituted alkyl chain; an optionally substituted alkenyl chain; an optionally substituted alkynyl chain; trihaloalkyl; $OR^6$; $NR^6R^7$; CN; $COR^6$; $CONR^6R^7$; $CO_2R^6$; $C(S)OR^6$; $OCONR^6R^7$; $OCOR^6$; $OCO_2R^6$; $OC(S)OR^6$; $NHCONR^6R^7$; $NHCOR^6$; $NR^6CO_2R^7$; $NHCO_2R^6$; $NHC(S)OR^6$; $NO_2$; $N_3$; $SR^6$; $SO_3H$; $SO_2R^6$; $SO_2NR^6R^7$ aryl; Het; an optionally substituted aryl linked by an optionally substituted alkyl, alkenyl, alkynyl chain, aryl or Het; or an optionally substituted heterocycle linked by an optionally substituted alkyl, alkenyl or alkynyl chain;

wherein x is one, two, three, four or five, independently of y, z;

wherein the phenyl ring bearing substituent $R^1$ is in an orto, meta or para position regarding the position "a" of the phenyl ring bearing substituent $R^2$ $R^2$ is hydrogen; OH; $NH_2$; SH; F; Cl; Br; I; methyl; an optionally substituted alkyl chain; an optionally substituted alkenyl chain; an optionally substituted alkynyl chain; trihaloalkyl; $OR^6$; $NR^6R^7$; CN; $COR^6$; $CONR^6R^7$; $CO_2R^6$; $C(S)OR^6$; $OCONR^6R^7$; $OCOR^6$; $OCO_2R^6$; $OC(S)OR^6$; $NO_2$; $N_3$; $NHCONR^6R^7$; $NHCOR^6$; $NR^6CO_2R^7$; $NHCO_2R^6$; $NHC(S)OR^6$; $NO_2$; $SO_3H$; $SO_2R^6$; $SO_2NR^6R^7$; aryl; Het; an optionally substituted aryl linked by an optionally substituted alkyl, alkenyl, alkynyl chain, aryl or Het; or an optionally substituted heterocycle linked by an optionally substituted alkyl, alkenyl or alkynyl chain;

wherein y is one, two, three, four or five, independently of x, z;

$R^3$ is hydrogen; OH; $NH_2$; SH; F; Cl; Br; I; methyl; an optionally substituted alkyl chain; an optionally substituted alkenyl chain; an optionally substituted alkynyl chain; trihaloalkyl; $OR^6$;

$NR^6R^7$; CN; $COR^6$; $CONR^6R^7$; $CO_2R^6$; $C(S)OR^6$; $OCONR^6R^7$; $OCOR^6$; $OCO_2R^6$; $OC(S)OR^6$; $NO_2$; $N_3$; $NHCONR^6R^7$; $NHCOR^6$; $NR^6CO_2R^7$; $NHCO_2R^6$; $NHC(S)OR^6$; $NO_2$; $SO_3H$; $SO_2R^6$; $SO_2NR^6R^7$; aryl; Het; an optionally substituted aryl linked by an optionally substituted alkyl, alkenyl, alkynyl chain, aryl or Het; or an optionally substituted heterocycle linked by an optionally substituted alkyl, alkenyl or alkynyl chain;

wherein z is one, two, three, four or five, independently of x, y;

$R^4$ is hydrogen; OH; $NH_2$; methyl; an optionally substituted alkyl chain; an optionally substituted alkenyl chain; an optionally substituted alkynyl chain; an optionally substituted cycloalkyl linked to S through an optionally substituted alkyl chain; an optionally substituted cycloalkyl linked to S through an optionally substituted alkenyl chain; an optionally substituted cycloalkyl linked to S through an optionally substituted alkynyl chain; an optionally substituted cycloalkenyl; an optionally substituted cycloalkenyl linked to S through an optionally substituted alkyl chain; an optionally substituted cycloalkenyl linked to S through an optionally substituted alkenyl chain; an optionally substituted cycloalkenyl linked to S through an optionally substituted alkynyl chain; an optionally substituted cycloalkynyl; an optionally substituted cycloalkynyl linked to S through an optionally substituted alkyl chain; an optionally substituted cycloalkynyl linked to S through an optionally substituted alkenyl chain; an optionally substituted cycloalkynyl linked to S through an optionally substituted alkynyl chain; trihaloalkyl; $OR^6$; $NR^6R^7$; CN; $COR^6$; $CONR^6R^7$; $CO_2R^6$; $C(S)OR^6$; $OCONR^6R^7$; $OCOR^6$; $OCO_2R^6$; $OC(S)OR^6$; $NO_2$; $N_3$; $NHCONR^6R^7$; $NHCOR^6$; $NR^6CO_2R^7$; $NHCO_2R^6$; $NHC(S)OR^6$; $NO_2$; $SO_3H$; $SO_2R^6$; $SO_2NR^6R^7$; aryl; Het; an optionally substituted aryl linked by an optionally substituted alkyl, alkenyl, alkynyl chain, aryl or Het; or an optionally substituted heterocycle linked by an optionally substituted alkyl, alkenyl or alkynyl chain;

$R^5$ is hydrogen; OH; $NH_2$; methyl; an optionally substituted alkyl chain; an optionally substituted alkenyl chain; an optionally substituted alkynyl chain; an optionally substituted cycloalkyl linked to N through an optionally substituted alkyl chain; an optionally substituted cycloalkyl linked to N through an optionally substituted alkenyl chain; an optionally substituted cycloalkyl linked to N through an optionally substituted alkynyl chain; an optionally substituted cycloalkenyl; an optionally substituted cycloalkenyl linked to N through an optionally substituted alkyl chain; an optionally substituted cycloalkenyl linked to N through an optionally substituted alkenyl chain; an optionally substituted cycloalkenyl linked to N through an optionally substituted alkynyl chain; an optionally substituted cycloalkynyl; an optionally substituted cycloalkynyl linked to N through an optionally substituted alkyl chain; an optionally substituted cycloalkynyl linked to N through an optionally substituted alkenyl chain; an optionally substituted cycloalkynyl linked to N through an optionally substituted alkynyl chain; trihaloalkyl; $OR^6$; $NR^6R^7$; CN; $COR^6$; $CONR^6R^7$; $CO_2R^6$; $C(S)OR^6$; $OCONR^6R^7$; $OCOR^6$; $OCO_2R^6$; $OC(S)OR^6$; $NO_2$; $N_3$; $NHCONR^6R^7$; $NHCOR^6$; $NR^6CO_2R^7$; $NHCO_2R^6$; $NHC(S)OR^6$; $NO_2$; $SO_3H$; $SO_2R^6$; $SO_2NR^6R^7$; aryl; Het; an optionally substituted aryl linked by an optionally substituted alkyl, alkenyl, alkynyl chain, aryl or Het; or an optionally substituted heterocycle linked by an optionally substituted alkyl, alkenyl or alkynyl chain;

$R^6$ and $R^7$ are selected, independently of each other, from hydrogen; methyl; an optionally substituted alkyl chain; an optionally substituted alkenyl chain; an optionally substituted alkynyl chain; an optionally substituted heterocycle; and an optionally substituted aryl, preferably phenyl or naphthyl;

each aryl as a group or part of a group is phenyl, naphthalenyl, anthracenyl, phenantrenyl, biphenyl, optionally fused to Het; each optionally substituted with one, two, three or four substituents selected from OH; F; Cl; Br; I; methyl; an optionally substituted alkyl chain; an optionally substituted alkenyl chain; an optionally substituted alkynyl chain; an optionally substituted cycloalkyl; an optionally substituted cycloalkenyl; an optionally substituted cycloalkynyl; $OR^6$; $NR^6R^7$; CN; $COR^6$; $CONR^6R^7$; $CO_2R^6$; $C(S)OR^6$; $OCONR^6R^7$; $OCOR^6$; $OCO_2R^6$; $OC(S)OR^6$; $N_3$; $NHCONR^6R^7$; $NHCOR^6$; $NR^6CO_2R^7$; $NHCO_2R^6$; $NHC(S)OR^6$; $NO_2$; $SR^6$; $SO_3H$; $SO_2R^6$; $SO_2NR^6R^7$; aryl; Het; an optionally substituted aryl linked by an optionally substituted alkyl, alkenyl, alkynyl chain, aryl or Het; and an optionally substituted heterocycle linked by an optionally substituted alkyl, alkenyl or alkynyl chain;

each Het as a group or part of a group is a monocyclic ring with 5, 6 or 7 ring atoms optionally fused to an aryl or a bicyclic ring structure comprising a 5, 6 or 7 membered ring linked to a 4, 5, or 6 membered ring; each of the rings being saturated, partially unsaturated, or completely unsaturated; at least one of the rings containing 1 to 5 heteroatoms each independently selected from nitrogen, oxygen and sulphur; and any one of the rings being optionally substituted with one, two, three or four substituents each independently selected from the group consisting of OH; F; Cl; Br; I; methyl; an optionally substituted alkyl chain; an optionally substituted alkenyl chain; an optionally substituted alkynyl chain; an optionally substituted cycloalkyl; an optionally substituted cycloalkenyl; an optionally substituted cycloalkynyl; $OR^6$; $NR^6R^7$; CN; $COR^6$; $CONR^6R^7$; $CO_2R^6$; $C(S)OR^6$; $OCONR^6R^7$; $OCOR^6$; $OCO_2R^6$; $OC(S)OR^6$; $N_3$; $NO_2$; $NHCONR^6R^7$; $NHCOR^6$; $NR^6CO_2R^7$; $NHCO_2R^6$; $NHC(S)OR^6$; $NO_2$; $SR^6$; $SO_3H$; $SO_2R^6$; $SO_2NR^6R^7$; aryl; Het; an optionally substituted aryl linked by an optionally substituted alkyl, alkenyl, alkynyl chain, aryl or Het; and an optionally substituted heterocycle linked by an optionally substituted alkyl, alkenyl or alkynyl chain;

for use in the prevention or treatment of cancer.

In a preferred embodiment, the phenyl ring bearing substituent $R^1$ is in para position regarding the position "a" of the phenyl ring bearing substituent $R^2$.

In another preferred embodiment, $R^3$ is hydrogen.

In a further preferred embodiment, $R^2$ is hydrogen; OH; $NH_2$; SH; F; Cl; Br; I; or methyl.

In a further preferred embodiment, $R^4$ is aryl; Het; an optionally substituted aryl linked by an optionally substituted alkyl, alkenyl, alkynyl chain, aryl or Het; or an optionally substituted heterocycle linked by an optionally substituted alkyl, alkenyl or alkynyl chain.

In a further preferred embodiment, $R^1$ is hydrogen; F; Cl; Br; I; methyl; an optionally substituted alkyl chain; $OR^6$; aryl; or Het;

$R^2$ is F; Cl; Br; I;

$R^5$ is hydrogen; methyl; an optionally substituted alkyl chain; an optionally substituted cycloalkyl linked to N through an optionally substituted alkyl chain; aryl; Het; an optionally substituted aryl linked by an optionally substituted alkyl, alkenyl, alkynyl chain, aryl or Het; or an optionally substituted heterocycle linked by an optionally substituted alkyl, alkenyl or alkynyl chain.

In a further preferred embodiment, $R^1$ is $OR^6$.

In a further preferred embodiment, $R^2$ is F.

In a further preferred embodiment, $R^4$ is aryl; Het; an optionally substituted aryl linked by an optionally substituted alkyl, alkenyl, alkynyl chain, aryl or Het; or an optionally substituted heterocycle linked by an optionally substituted alkyl, alkenyl or alkynyl chain; In a further preferred embodiment, $R^5$ is H.

It should be noted that each of the previous embodiments can be considered independently from each other or each embodiment can be combined with one or more of the other embodiments.

In an even further preferred embodiment, the compound of formula (I) is selected from the compounds of table 1:

TABLE 1

| CODE | R1 | R2 | R3 | R4 | R5 | x y z |
|---|---|---|---|---|---|---|
| IUCT-0460 | OMe | F | H | 4,5-dichlorothiophen-2-yl | H | 1 1 1 |
| IUCT-0461 | OMe | F | H | 3,5-dimethylisoxazol-4-yl | H | 1 1 1 |
| IUCT-0462 | OMe | F | H | benzo[d][1,3]dioxol-5-yl | H | 1 1 1 |
| IUCT-0463 | OMe | F | H | 5-(pyridin-2-yl)thiophen-2-yl | H | 1 1 1 |
| IUCT-0464 | OMe | F | H | benzofuran-2-yl | H | 1 1 1 |
| IUCT-0465 | OMe | F | H | 4,5-dichlorothiophen-2-yl | CH$_2$CN | 1 1 1 |
| IUCT-0466 | OMe | F | H | benzo[d][1,3]dioxol-5-yl | CH$_2$CO$_2$Et | 1 1 1 |
| IUCT-0467 | OMe | F | H | benzo[d][1,3]dioxol-5-yl | CH$_2$C(O)-morpholinyl | 1 1 1 |
| IUCT-0468 | OMe | F | H | 4,5-dichlorothiophen-2-yl | CH$_2$CONH$_2$ | 1 1 1 |
| IUCT-0469 | OMe | F | H | 5-(pyridin-2-yl)thiophen-2-yl | CH$_2$CO$_2$Et | 1 1 1 |

TABLE 2

| CODE | IUPAC NAME |
|---|---|
| IUCT-0460 | 4,5-Dichloro-N-(1-(3-fluoro-2'-methoxy-[1,1'-biphenyl]-4-yl)-2-oxopiperidin-3-yl)thiophene-2-sulfonamide |
| IUCT-0461 | N-(1-(3-fluoro-2'-methoxy-[1,1'-biphenyl]-4-yl)-2-oxopiperidin-3-yl)-3,5-dimethylisoxazole-4-sulfonamide |
| IUCT-0462 | N-(1-(3-fluoro-2'-methoxy-[1,1'-biphenyl]-4-yl)-2-oxopiperidin-3-yl)benzo[d][1,3]dioxole-5-sulfonamide |
| IUCT-0463 | N-(1-(3-fluoro-2'-methoxy-[1,1'-biphenyl]-4-yl)-2-oxopiperidin-3-yl)-5-(pyridin-2-yl)thiophene-2-sulfonamide |
| IUCT-0464 | N-(1-(3-fluoro-2'-methoxy-[1,1'-biphenyl]-4-yl)-2-oxopiperidin-3-yl)benzofuran-2-sulfonamide |
| IUCT-0465 | 4,5-Dichloro-N-(cyanomethyl)-N-(1-(3-fluoro-2'-methoxy-[1,1'-biphenyl]-4-yl)-2-oxopiperidin-3-yl)thiophene-2-sulfonamide |
| IUCT-0466 | Ethyl N-(benzo[d][1,3]dioxol-5-ylsulfonyl)-N-(1-(3-fluoro-2'-methoxy-[1,1'-biphenyl]-4-yl)-2-oxopiperidin-3-yl)glycinate |
| IUCT-0467 | N-(1-(3-fluoro-2'-methoxy-[1,1'-biphenyl]-4-yl)-2-oxopiperidin-3-yl)-N-(2-morpholino-2-oxoethyl)benzo[d][1,3]dioxole-5-sulfonamide |
| IUCT-0468 | 2-((4,5-dichloro-N-(1-(3-fluoro-2'-methoxy-[1,1'-biphenyl]-4-yl)-2-oxopiperidin-3-yl)thiophene)-2-sulfonamido)acetamide |
| IUCT-0469 | Ethyl N-(1-(3-fluoro-2'-methoxy-[1,1'-biphenyl]-4-yl)-2-oxopiperidin-3-yl)-N-((5-(pyridin-2-yl)thiophen-2-yl)sulfonyl)glycinate |

Preferably, the compound of formula (I) is N-(1-(3-fluoro-2'-methoxy-[1,1'-biphenyl]-4-yl)-2-oxopiperidin-3-yl)-5-(pyridin-2-yl)thiophene-2-sulfonamide.

Unless specifically stated when defining the radicals (R) in the compound of formula (I), for the purposes of present description, the following terms are further defined as follows and applied as such.

The terms "heterocyclic ring" or "heterocycle" are used interchangeably herein and refer to any compound in which plurality of atoms form a ring via a plurality of covalent bonds, wherein the ring includes at least one atom other than a carbon atom. Particularly contemplated heterocyclic bases include 4-, 5- and 6-membered rings containing at least 1 to 4 heteroatoms each independently selected from nitrogen, oxygen and sulphur as the non-carbon atom (e.g., imidazole, pyrrole, triazole, dihydropyrimidine). Further contemplated heterocycles may be fused (i.e., covalently bound) to another ring or heterocycle, and are thus termed "fused heterocycle" or "fused heterocyclic base" as used herein. Especially contemplated fused heterocycles include a 5-membered ring fused to a 6-membered ring (e.g., purine, pyrrolo[2,3-d]pyrimidine), and a 6-membered ring fused to another 6-membered or higher ring (e.g., pyrido[4,5-d]pyrimidine, benzodiazepine). Still further contemplated heterocyclic bases may be aromatic, or may include one or more double or triple bonds. Moreover, contemplated heterocyclic bases and fused heterocycles may further be substituted in one or more positions. And any one of the rings being optionally substituted with one, two or three substituents each independently selected from the group consisting of halogen, hydroxy, nitro, cyano, carboxyl, $C_{1-6}$alkyl, $C_{1-6}$alkoxy, $C_{1-6}$alkoxy$C_{1-6}$alkyl, $C_{1-6}$alkylcarbonyl, amino, mono- or di$C_{1-6}$alkylamino, azido, mercapto, polyhalo$C_{1-6}$alkyl, polyhalo$C_{1-6}$alkoxy, and $C_{3-7}$cycloalkyl.

"Het" is defined herein as a group or part of a group being a monocyclic ring with 5, 6 or 7 ring atoms optionally fused to an aryl or a bicyclic ring structure comprising a 5, 6 or 7 membered ring linked to a 4, 5, or 6 membered ring; each of the rings being saturated, partially unsaturated, or completely unsaturated; at least one of the rings containing 1 to 5 heteroatoms each independently selected from nitrogen, oxygen and sulphur; and any one of the rings being optionally substituted with one, two, three or four substituents each independently selected from the group consisting of OH; F; Cl; Br; I; methyl; an optionally substituted alkyl chain; an optionally substituted alkenyl chain; an optionally substituted alkynyl chain; an optionally substituted cycloalkyl; an optionally substituted cycloalkenyl; an optionally substituted cycloalkynyl; $OR^6$; $NR^6R^7$; CN; $COR^6$; $CONR^6R^7$; $CO_2R^6$; $C(S)OR^6$; $OCONR^6R^7$; $OCOR^6$; $OCO_2R^6$; $OC(S)OR^6$; $N_3$; $NO_2$; $NHCONR^6R^7$; $NHCOR^6$; $NR^6CO_2R^7$; $NHCO_2R^6$; $NHC(S)OR^6$; $NO_2$; $SR^6$; $SO_3H$; $SO_2R^6$; $SO_2NR^6R^7$; aryl; Het; an optionally substituted aryl linked by an optionally substituted alkyl, alkenyl, alkynyl chain, aryl or Het; and an optionally substituted heterocycle linked by an optionally substituted alkyl, alkenyl or alkynyl chain.

The term "tautomer" or "tautomeric form" refers to structural isomer of different energies which are interconvertible via a low energy barrier. For example, proton tautomers (also known as prototropic tautomers) include interconversion via migration of a proton, such as keto-enol and imine-enamine isomerizations. Valence tautomers include interconversions by reorganization of some of the bonding electrons.

The term "regioisomer" refers to structural isomer, or constitutional isomer in the sense that refers to molecules with the same molecular formula that whose atoms are bonded in different order of connectivity.

The term "conversion" refers to is the percentage of starting material that is transformed into products, either the expected final product, byproducts, or even into products of degradation.

The term "yield" is the number of synthesized molecules of product per number of starting molecules. In a multistep synthesis, the yield can be calculated by multiplication of the yields of all the single steps.

The term "anomeric purity" refers to the amount of a particular anomer of a compound divided by the total amount of all anomers of that compound present in the mixture multiplied by 100.

The term "intermediate" or "intermediates" refer to any compounds which may be transformed into the final product by means of suitable additional chemical reactions. The compounds of the present invention can also be considered as intermediate compounds and as such are also included in the scope of the present invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

For therapeutic use, salts the compounds of formula (I) are those wherein the counter-ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the scope of the present invention.

The pharmaceutically acceptable acid and base addition salts as mentioned above are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which either the compounds of formula (I) as well as the salts thereof, are able to form. Such solvates are for example hydrates, alcoholates and the like.

The term "quaternary amine" as used hereinbefore defines the quaternary ammonium salts which the compounds of formula (I) are able to form by reaction between a basic nitrogen of either the compounds of formula (I) or the compounds of formula (I)I and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several nitrogen atoms are oxidized to the so-called N-oxide.

It will be appreciated that the compounds of formula (I) may have metal binding, chelating, complex forming properties and therefore may exist as metal complexes or metal chelates. Such metalated derivatives of the compounds of formula (I) are intended to be included within the scope of the present invention.

Some of the compounds of the compounds of formula (I) may also exist in their tautomeric form. Such forms although not explicitly indicated in the above formula are intended to be included within the scope of the present invention.

The compounds described herein may have asymmetric centers and occur as racemates, racemic mixtures, individual diastereomers or enantiomers, with all isomeric forms being included in the present invention. Compounds of the present invention having a chiral center can exist in and be isolated in optically active and racemic forms. Some compounds can exhibit polymorphism.

The term "alkyl" as used herein it does refer to any linear, branched, or cyclic hydrocarbon in which all carbon-carbon bonds are single bonds. Alkyl chains may optionally be substituted by OH; $NH_2$; F; Cl; Br; I; methyl; an optionally substituted alkyl chain; an optionally substituted alkenyl chain; an optionally substituted alkynyl chain; an optionally substituted cycloalkyl; an optionally substituted cycloalkenyl; an optionally substituted cycloalkynyl; $OR_6$; $NR_6R_7$; CN; $COR_6$; $CONR_6R_7$; $CO_2R_6$; $C(S)OR_6$; $OCONR_6R_7$; $OCOR_6$; $OCO_2R_6$; $OC(S)OR_6$; $N_3$; $NO_2$; $NHCONR_6R_7$; $NHCOR_6$; $NR_6CO_2R^7$; $NHCO_2Re$; $NHC(S)OR_6$; $NO_2$; $SR_6$; $SO_3H$; $SO_2R_6$; $SO_2NR_6R_7$; aryl; Het; an optionally substituted aryl linked by an optionally substituted alkyl, alkenyl, alkynyl chain, aryl or Het; and an optionally substituted heterocycle linked by an optionally substituted alkyl, alkenyl or alkynyl chain.

The term "alkenyl" and "optionally substituted alkenyl" are used interchangeably herein and refer to any linear, branched, or cyclic alkyl with at least one carbon-carbon double bond. Alkenyl chains may optionally be substituted by OH; $NH_2$; F; Cl; Br; I; methyl; an optionally substituted alkyl chain; an optionally substituted alkenyl chain; an optionally substituted alkynyl chain; an optionally substituted cycloalkyl; an optionally substituted cycloalkenyl; an optionally substituted cycloalkynyl; $OR_6$; $NR_6R_7$; CN; $COR_6$; $CONR_6R_7$; $CO_2Re$; $C(S)OR_6$; $OCONR_6R_7$; $OCOR_6$; $OCO_2Re$; $OC(S)OR_6$; $N_3$; $NO_2$; $NHCONR_6R_7$; $NHCOR_6$; $NR_6CO_2R^7$; $NHCO_2Re$; $NHC(S)OR_6$; $NO_2$; $SR_6$; $SO_3H$; $SO_2Re$; $SO_2NR_6R_7$; aryl; Het; an optionally substituted aryl linked by an optionally substituted alkyl, alkenyl, alkynyl chain, aryl or Het; and an optionally substituted heterocycle linked by an optionally substituted alkyl, alkenyl or alkynyl chain.

Furthermore, the term "alkynyl" and "optionally substituted alkynyl" are used interchangeably herein and refer to any linear, branched, or cyclic alkyl or alkenyl with at least one carbon-carbon triple bond. Alkynyl chains may optionally be substituted by OH; $NH_2$; F; Cl; Br; I; methyl; an optionally substituted alkyl chain; an optionally substituted alkenyl chain; an optionally substituted alkynyl chain; an optionally substituted cycloalkyl; an optionally substituted cycloalkenyl; an optionally substituted cycloalkynyl; $OR_6$; $NR_6R_7$; CN; $COR_6$; $CONR_6R_7$; $CO_2R_6$; $C(S)OR_6$; $OCONR_6R_7$; $OCOR_6$; $OCO_2R_6$; $OC(S)OR_6$; $N_3$; $NO_2$; $NHCONR_6R_7$; $NHCOR_6$; $NR_6CO_2R^7$; $NHCO_2Re$; $NHC(S)OR_6$; $NO_2$; $SR_6$; $SO_3H$; $SO_2Re$; $SO_2NR_6R_7$; aryl; Het; an optionally substituted aryl linked by an optionally substituted alkyl, alkenyl, alkynyl chain, aryl or Het; and an optionally substituted heterocycle linked by an optionally substituted alkyl, alkenyl or alkynyl chain.

The term "aryl" as used herein is a group or part of a group being phenyl, naphthalenyl, anthracenyl, phenantrenyl, biphenyl, optionally fused to Het; each optionally substituted with one, two, three or four substituents selected from OH; F; Cl; Br; I; methyl; an optionally substituted alkyl chain; an optionally substituted alkenyl chain; an optionally substituted alkynyl chain; an optionally substituted cycloalkyl; an optionally substituted cycloalkenyl; an optionally substituted cycloalkynyl; $OR^6$; $NR^6R^7$; CN; $COR^6$; $CONR^6R^7$; $CO_2R^6$; $C(S)OR^6$; $OCONR^6R^7$; $OCOR^6$; $OCO_2R^6$; $OC(S)OR^6$; $N_3$; $NHCONR^6R^7$; $NHCOR^6$; $NR^6CO_2R^7$; $NHCO_2R^6$; $NHC(S)OR^6$; $NO_2$; $SR^6$; $SO_3H$; $SO_2R^6$; $SO_2NR^6R^7$; aryl; Het; an optionally substituted aryl linked by an optionally substituted alkyl, alkenyl, alkynyl chain, aryl or Het; and an optionally substituted heterocycle linked by an optionally substituted alkyl, alkenyl or alkynyl chain.

The term "substituted" as used herein refers to a replacement of an atom or chemical group (e.g., H, $NH_2$, or OH) with a functional group, and particularly contemplated functional groups include nucleophilic groups (e.g., $-NH_2$, $-OH$, $-SH$, $-NC$, etc.), electrophilic groups (e.g., C(O) OR, C(X)OH, etc.), polar groups (e.g., $-OH$) non-polar groups (e.g., aryl, alkyl, alkenyl, alkynyl, etc.), ionic groups (e.g., $-NH_3^+$), and halogens (e.g., $-F$, $-Cl$), and all chemically reasonable combinations thereof. Thus, the term "functional group" and the term "substituent" are used interchangeably herein and refer to nucleophilic groups (e.g., $-NH_2$, $-OH$, $-SH$, $-NC$, $-CN$, etc.), electrophilic groups (e.g., C(O)OR, C(X)OH, C(Halogen)OR, etc.), polar groups (e.g., $-OH$), non-polar groups (e.g., aryl, alkyl, alkenyl, alkynyl, etc.), ionic groups (e.g., $-NH_3^+$), and halogens. Functional groups such as $-OH$, $-NH_2$, and the like, can incorporate protecting groups (abbreviated as PG) such as those known for those skilled in the art (GREENE'S *PROTECTIVE. GROUPS IN ORGANIC. SYNTHESIS.* Fourth Edition. PETER G. M. WUTS. and. THEODORA W. GREENE. 2007. Wiley-Interscience). By way of example, hydroxyl protection (Greene's vide supra, pages 16-366), including 1,2-diols could be in the form of ethers, esters, cyclic acetals, cyclic ketals, and silyl derivatives, such as, but not limited to, methyl ether, methoxymethyl ether, methylthiomethyl ether, t-butylthiomethyl ether, (phenyldimethylsislymethoxymethyl) ether, benzyloxymethyl ether, p-methoxybenzyloxymethyl ether, p-nitrobenzyloxymethyl ether, o-nitrobenzyzloxymethyl ether, (4-methoxyphenoxy) methyl ether, guaiacolmethyl ether, t-butoxymethyl ether, 4-pentenyloxymethyl ether, siloxymethyl ether, 2-methoxethoxymethyl ether, 2,2,2-trichloroethoxymethyl ether, bis(2-chloroethoxy)methyl ether, 2-(trimethylsilyl) ethoxymethyl ether, menthoxymethyl ether, tetrahydropyranyl ether, 3-bromotetrahydropyranyl ether, tetrahydrothiopyranyl ether, 1-methoxycyclohexyl ether, 4-methoxytetrahydropyranyl ether, 4-methoxytetrahydrothiopyranyl ether, 4-methoxytetrahydrothiopyranyl S, S-Dioxido ether, 1-[(2-chloro-4-methyl)phenyl]-4-methoxypiperidin-4-yl ether, 1,4-dioxan-2-yl ether, 1,4-dioxan-2-yl ether, tetrahydrothiofuranyl ether, 2,3,3a,4,5,6,7,7a-octahydro-7,8,8-trimethyl-4,7-methanobenzofuran-2-yl ether, 1-ethoxyethyl ether, 1-(2-chloroethoxy)ethyl ether, 1-hydroxyethyl ether, 2-bromoethyl ether, 1-[2-(trimethylsilyl) ethoxy]ethyl ether, 1-(2-cyanoethoxy)ethyl ether, prenyl ether, cynnamyl ether, propargyl ether, p-nitrophenyl ether, 1-methyl-1-methoxyethyl ether, 1-methyl-1-benzyloxyethyl ether, 1-methyl-1-1-benzyloxy-2-fluoroethyl ether, 2,2,2-trichloroethyl ether, 2-trimethylsilylethyl ether, 2-(phenylselenyl)ethyl ether, t-butyl ether, allyl ether, p-chlorophenyl ether, p-methoxyphenyl ether, 2,4-dinitrophenyl ether, benzyl ether, p-methoxylbenzyl ether, 3,4-dimethoxybenzyl ether, 2,6-dimethoxybenyzl, o-nitrobenzyl ether, p-nitrobenzyl ether, p-bromobenzyl ether, p-chlorobenzyl ether, 2,6-dichlorobenzyl ether, 2,4-dinitrobenzyl ether, fluorous benzyl ether, trimethylsilylxylyl ether, p-phenylbenzyl ether, cumyl ether, p-azidobenzyl ether, 2,6-difluorobenzyl ether, p-cyanobenzyl ether, p-phenylbenzyl ether, 2-picolyl ether, 4-picolyl ether, 3-methyl-2-picolyl N-oxido ether, diphenylmethyl ether, p,p'-dinitrobenzhydryl ether, 5-dibenzosuberyl ether, triphenylmethyl ether, α-naphtyldiphenylmethyl ether, p-methoxyphenyldiphenylmethyl ether, di(p-methoxyphenyl)phenylmethyl ether, tri(p-methoxyphenyl) phenylmethyl ether, 4-(4'-bromophenacyloxyphenyl)diphenylmethyl ether, 4,4',4"-tris(4,5-dichlorophthalimidophenyl) methyl ether, pentadienylnitrobenzyl, p-azidobenzyl ether, p-(methylsulfinyl)benzyl ether, 2-naphthylmethyl ether, 2-quinolinylmethyl ether, 1-pyrenylmethyl ether, 4-methoxydiphenylmethyl ether, 4-phenyldiphenylmethyl ether, α-naphthyldiphenylmethyl ether, p-methoxyphenyldiphenylmethyl ether, anthryl ether, 9-phenylthioxanthyl ether and the like; Silyl ethers such as trimethylsilyl ether, triethylsilyl ether, triisopropylsilyl ether, dimethylhexylsilyl ether, 2-norbornyldimethylsilyl ether, t-butyldimethylsilyl ether, t-butyldiphenylsilyl ether, tribenzylsilyl ether, tri-p-xylylsilyl ether, triphenylsilyl ether, diphenylmethylsilyl ether, di-t-butylmethylsilyl ether, bis(t-butyl)-1-pyrenylmethoxysilyl ether, tris(trimethylsilyl)silyl ether, (2-hidroxystyryl)dimethylsilyl ether, t-butoxydiphenylsilyl ether, 1,1,3,3-tetraisopropyl-3-[2-(tripheynlmethoxy)ethoxy] disiloxane-1-yl ether, fluorous silyl ether, and the like; Esters such as formate, benzoylformate, acetate, chloroacetate, dichloroacetate, trichloroacetate, trichloroacetimidate, trifluoroacetate, methoxyacetate, triphenylmethoxyacetate, phenoxyacetate, p-chloropheynyacetate, phenylacetate, diphenylacetate, 3-phenylpropionate, bisfluorous chain type propanoyl ester, 4-pentenoate, levulinate, pivaloate, adamantoate, crotonate, 4-methoxylcrotonate, benzoate, p-phenylbenzoate, mesitoate, 4-bromobenzoate, 2,5-diflourobenzoate, p-nitrobenzoate, picolinate, nicotinate, 2-(azidomethyl)benzoate, 4-azidobutirate, (2-azidomethyl) phenylacetate, 2-{[(tritylthio)oxy]methyl}benzoate, 2-(allyloxy)phenylacetate, 2-(prenyloxymethyl)benzoate, 4-benzyloxybutyrate, 4-trialkylsiloxybutyrate, 4-acetoxy-2,2-dimethylbutyrate, 2,2-dimethyl-4-pentanoate, 2-iodobenzoate, 4-nitro-4-methylpentanoate, o-(dibromomethyl)benzoate, 2-formylbenzenesulfonate, 4-(methylthiomethoxy)butyrate, 2-(methylthiomethoxymethyl)benzoate, 2-(chloroacetoxymethyl)benzoate, 2-[(2-chloracetoxy) ethyl]benzoate, 2-[2-(benzyloxy)ethyl]benzoate, 2-[2-(4-methoxybenzyloxy)ethyl]benzoate, 2,6-dichloro-4-methylphenoxyacetate, 2,6-dichloro-4-(1,1,3,3-tetramethylbutyl) phenoxyacetate, chlorodiphenylacetate, isobutyrate, monosuccionate, tigloate, o-(methoxycarbonyl)benzoate, p-benzoate, α-napthoate, nitrate, alkyl N,N,N',N'-tetramethylphosphorodiamidate, 2-chlorobenzoate, and the like; Sulfonates such as sulfate, allylsulfonate, methanesulfonate, benzylsulfonate, tosylate, 2-trifluoromethylsulfonate and the like; Carbonates such as alkyl methyl carbonate, methoxymethyl carbonate, 9-fluoromethyl carbonate, ethyl carbonate, bromoethyl carbonate, 2-(trimethylsilyl)ethyl carbonate, isobutyl carbonate, t-butyl carbonate, vinyl carbonate, allyl carbonate, propargyl carbonate, p-nitrophenyl carbonate, benzyl carbonate, 2-dansylethyl carbonate, phenacyl carbonate, methyl dithiocarbonate, S-benzyl thiocarbonate and the like; Carbamates such as dimethylthiocarbamate, N-phenylcarbamate, and the like; Cyclic acetals and ketals such as methylene acetal, ethylidene acetal, t-butylmethylidene acetal, 1-t-butylethylidine ketal, 1-phenyethylidene ketal, 2-(methoxycarbonyl)ethylidene acetal, 2-(t-butylcarbonyl) ethylidene acetal, phenylsulfonylethylidene acetal, 3-(benzyloxy)propylidene acetal, isopropylidene acetal or acetonide, cyclopentylidene acetal, benzylidene acetal, p-methoxybenzylidene acetal, mesitylene acetal, naphthaldehyde acetal, 9-anthracene acetal, benzophenone ketal and the like; Chiral ketones such as camphor ketal, menthone ketal and the like; Cyclic ortho esters such as methoxymethylene acetal, ethoxymethylene acetal, dimethoxymethylene orto ester, methylidene orto ester, phthalide orto ester, 1,2-dimethoxyethylidene orto ester, 2-oxacyclopentylidene orto ester, butane 2,3-bisacetal, cyclohexane-1,2-diacetal, dispiroketals and the like; Silyl derivatives such as di-t-butylsilylene group, diakkylsilylene group, 1,3-(1,1,3,3-tetraisopropyldisiloxanylidene) derivative, 1,1,3,3-tetra-t-butoxydisiloxanylidene derivative, methylene-bis-(diisopropylsilanoxanylidene, 1,1,4,4-tetrapheynyl-1,4-disilanylidene, o-xylyl ether, 3,3'-oxybis(dimethoxytrityl) ether, and the like; cyclic carbonates; cyclic borate such as methyl boronate, ethyl boronate, and the like.

The term "optionally substituted" when referring to alkyl, alkenyl, alkynyl, cycloalkyl, cycloalkenyl, aryl and heterocycle is intended to cover groups having oxo, ethylenedioxy, alkanoyloxy, alkoxy, alkylthio, carboxyl, halogen, thienyl, acetyl, 1-oxopropyl, 2-oxopropyl, 2-oxobutyl, 3-oxobutyl, 3-oxopentyl, 4-oxopentyl, 4-oxohexyl, 5-oxohexyl, ethylenedioxymethyl, 1,1-ethylenedioxyethyl, 2,2-ethylenedioxyethyl, 1,1-ethylenedioxypropyl, 2,2-ethylenedioxypropyl, 3,3-ethylenedioxypropyl, 1,1-ethylenedioxybutyl, 2,2-ethylenedioxybutyl, 3,3-ethylenedioxybutyl, 4,4-ethylenedioxybutyl, 3,3-ethylenedioxypentyl, 4,4-ethylenedioxyhexyl, 5,5-ethylenedioxyhexyl, acetyloxymethyl, 2-acetyloxyethyl, 3-acetyloxypropyl, 3-acetyloxybutyl, 4-acetyloxybutyl, 3-propionyloxybutyl, 3-butyryloxybutyl, 3-valeryloxypentyl, 3-hexanoyloxyhexyl, 4-acetyloxypentyl, 5-acetyloxypentyl, 4-acetyloxyhexyl, 5-acetyloxyhexyl, 6-acetyloxyhexyl, methoxymethyl, ethoxymethyl, propoxymethyl, butoxymethyl, pentyloxymethyl, hexyloxymethyl, 1-methoxyethyl, 2-methoxyethyl, 2-ethoxyethyl, 2-propoxyethyl, 2-butoxyethyl, 2-pentyloxyethyl, 2-hexyloxyethyl, 3-methoxypropyl, 3-ethoxypropyl, 2-methoxybutyl, 4-ethoxybutyl, 3-methoxypentyl, 5-ethoxypentyl, 4-methoxyhexyl, 6-ethoxyhexyl, methylthiomethyl, ethylthiomethyl, propylthiomethyl, butylthiomethyl, pentylthiomethyl, hexylthiomethyl, 1-methylthioethyl, 2-methylthioethyl, 2-ethylthioethyl, 2-methylthiopropyl, 3-methylthiopropyl, 3-ethylthiobutyl, 4-butylthiobutyl, 5-methylthiopentyl, 6-ethylthiohexyl, carboxymethyl, 1-carboxyethyl, 2-carboxyethyl, 2-carboxypropyl, 3-carboxypropyl, 4-carboxybutyl, 5-carboxypentyl, 6-carboxyhexyl, fluoromethyl, bromomethyl, chloromethyl, iodomethyl, 2-chloroethyl, 2-bromopropyl, 3-iodopropyl, 4-fluorobutyl, 5-chloropentyl, 6-bromohexyl, 2-thienylmethyl, 1-(2-thienyl)ethyl, 2-(2-thienyl)ethyl and the like.

The term "amino acid" refers to any of a class of organic compounds that contains at least one amino group, —NH—, and one carboxyl group, —COOH. These compounds can be the natural amino acids present in peptides or can contain any substitution in the amino group, in the carboxyl group or in the side chain. They can also present different chirality of the peptidic natural amino acids or can have different backbone, linear or cyclic, but must present, as said, at least one amino group and one carboxyl group. Amino acids can incorporate functional or protecting groups, such as those known for those skilled in the art (T. W. Greene, vide supra). Preferred amino acids include, but are not limited to, alanine, valine, leucine and isoleucine.

In a preferred embodiment, the compound of formula (I), according to any of the above embodiments, being alone or combined, is for use in preventing and/or treating a cancer in a subject, being said cancer selected from basal cell carcinoma, melanoma, medulloblastoma, astrocytoma, lung cancer, prostate cancer, pancreatic cancer, colorectal cancer, breast cancer, ovarian cancer, cervical cancer, glioblastoma, neuroblastoma, digestive tract tumors, leukemia, rhabdomyosarcoma and osteosarcoma. Preferably the subject is a human subject.

The present disclosure also relates to a method of prevention or treatment of cancer, preferably selected from basal cell carcinoma, melanoma, medulloblastoma, astrocytoma, lung cancer, prostate cancer, pancreatic cancer, colorectal cancer, breast cancer, ovarian cancer, cervical cancer, glioblastoma, neuroblastoma, digestive tract tumors, leukemia, rhabdomyosarcoma and osteosarcoma in a subject comprising administering to said subject a therapeutically effective amount of the compound of formula (I), according to any of the above embodiments, as defined above in any of the possible embodiments. Preferably the subject is a human subject.

The present disclosure also related to the use of a compound of formula (I), according to any of the above embodiments, in the manufacture of a medicament for the treatment or prevention of cancer in a subject, preferably selected from basal cell carcinoma, melanoma, medulloblastoma, astrocytoma, lung cancer, prostate cancer, pancreatic cancer, colorectal cancer, breast cancer, ovarian cancer, cervical cancer, glioblastoma, neuroblastoma, digestive tract tumors, leukemia, rhabdomyosarcoma and osteosarcoma. Preferably the subject is a human subject.

In another embodiment the compound of formula (I), according to any of the above embodiments, is combined with a further compound selected from a chemotherapeutic agent; an antimetabolite; a spindle poison plant alkaloid; a cytotoxic/antitumour antibiotic; a topoisomerase inhibitor; an antibody; a photosensitizer; a kinase inhibitor; a pathway-specific inhibitor (e.g. Notch pathway-inhibitors); an anti-hormonal agent; an aromatase inhibitor; an anti-androgen; a ribozyme; a vaccine; an anti-angiogenic agent; an antiviral agent; or a combination thereof.

In another embodiment, the compound of formula (I), according to any of the above embodiments, is included in a pharmaceutical composition.

In another embodiment, the compound of formula (I), according to any of the above embodiments, is to be administered by oral, rectal, nasal, ocular, topical, vaginal, parenteral, transdermal, intraperitoneal, intrapulmonary or intranasal route.

In another embodiment, the compound of formula (I), according to any of the above embodiments, is used in the prevention or treatment of cancer combined with surgical therapy, radiotherapy, immunotherapy (for example based on antibodies or immunologic cells), epigenetic therapy (using for example methyltransferase inhibitors, histone deacetylase inhibitors, miRNAs) or a combination thereof.

The following Examples are offered for illustrative purposes only and are not intended to limit the scope of the present invention in any way.

EXAMPLES

Example 1

The compounds designated in table 1 as IUCT-0460, IUCT-0462, IUCT-0463, IUCT-0467 and IUCT-0469 (all covered by the formula (I)) showed better anti-proliferative activity than the reference compound Vismodegib in the rhabdomyosarcoma cell line RH4. The measurements were taken using an in vitro test to measure cell growth based on Methyl violet staining after 5 days of incubation with the aforementioned drugs or control vehicle (DMSO). The procedure was carried out in a 96-well plate and cells were fixed for 30 minutes with 4% paraformaldehyde (PFA) at room temperature. After 3 washes with phosphate-buffered saline (PBS), cells were stained for 30 minutes at room temperature with Methyl violet (dilution 1/25 of a stock solution made with 1.5% w/v in PBS). After 5 washes, and the addition of acetic acid (15% in water), plates were read in a spectrophotometer at 590 nm. All conditions were tested in 8 independent wells and results expressed as a mean of all replicates (FIG. 1).

Figure 2:
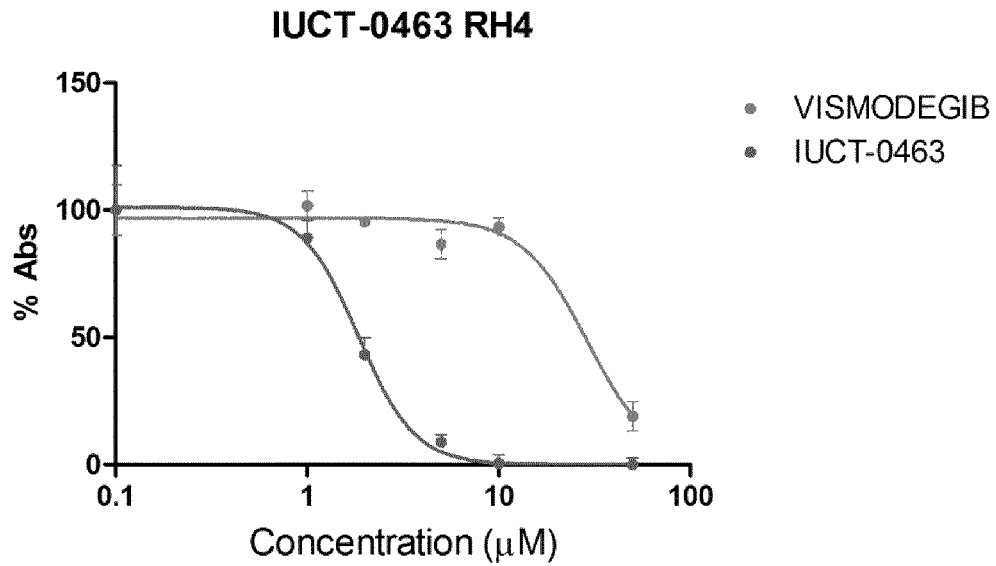
FIG. 2 depicts the dose-response curves of the most active compound IUCT-0463 and the reference compound Vismodegib in the rhabdomyosarcoma cell line RH4.

Additional measurements using the same procedure were made specifically for the compound IUCT-0463 to obtain a dose-response curve from 1 to 50 μM in the cell line RH4. The curve obtained for cells treated with IUCT-0463 showed a clear improvement of the anti-tumor activity when compared to the reference compound Vismodegib (FIG. 2)

Example 2

Figure 3:
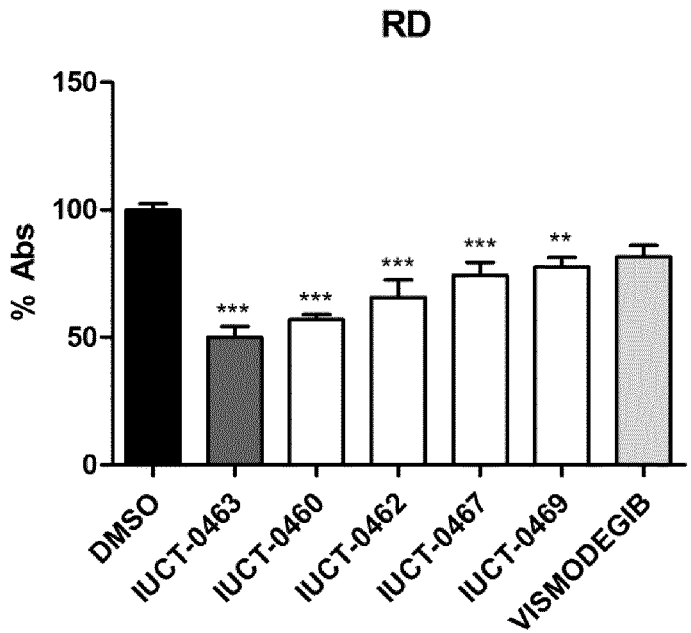
FIG. 3 represents the effects (in percentage with respect to the vehicle control DMSO) of five compounds according to formula (I) (IUCT-0460, IUCT-0462, IUCT-0463, IUCT-0467, IUCT-0469) and the reference compound Vismodegib on cell growth of RD rhabdomyosarcoma cells after 5 day incubation (mean+/−SD). All compounds were used at a concentration of 10 microM. Statistical analysis was performed using ANOVA. As statistical differences were observed (p=0), the pairwise comparison against the vehicle control was made using the Tukey test. Notation: *=statistically-significant difference with a p-value<0.001, =p-value<0.01 and *=p-value<0.05.

The compounds designated in table 1 as IUCT-0460, IUCT-0462, IUCT-0463, IUCT-0467 and IUCT-0469 (all covered by the formula (I)) showed better anti-proliferative activity than the reference compound Vismodegib in the rhabdomyosarcoma cell line RD. The measurements were taken using an in vitro test to measure cell growth based on Methyl violet staining after 5 days of incubation with the aforementioned drugs or control vehicle (DMSO). The procedure was carried out in a 96-well plate and cells were fixed for 30 minutes with 4% paraformaldehyde (PFA) at room temperature. After 3 washes with phosphate-buffered saline (PBS), cells were stained for 30 minutes at room temperature with Methyl violet (dilution 1/25 of a stock solution made with 1.5% w/v in PBS). After 5 washes, and the addition of acetic acid (15% in water), plates were read in a spectrophotometer at 590 nm. All conditions were tested in 8 independent wells and results expressed as a mean of all replicates (FIG. 3).

Figure 4:
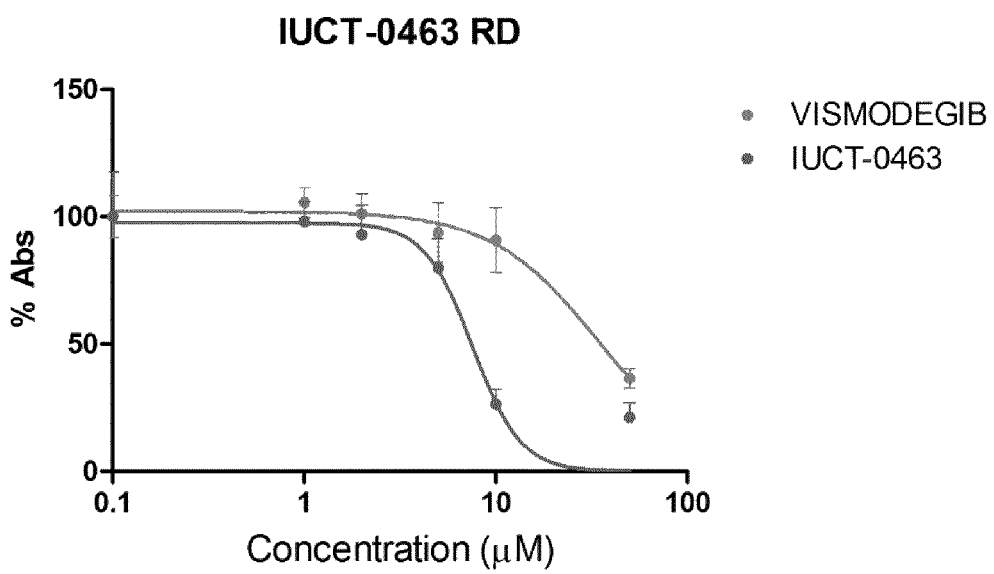
FIG. 4 depicts the dose-response curves of the most active compound IUCT-0463 and the reference compound Vismodegib in the rhabdomyosarcoma cell line RD.

Additional measurements using the same procedure were made specifically for the compound IUCT-0463 to obtain a dose-response curve from 1 to 50 μM in the cell line RD. The curve obtained in cells treated with IUCT-0463 showed a clear improvement of the anti-tumor activity when compared to the reference compound Vismodegib (FIG. 4)

Example 3

Figure 5:
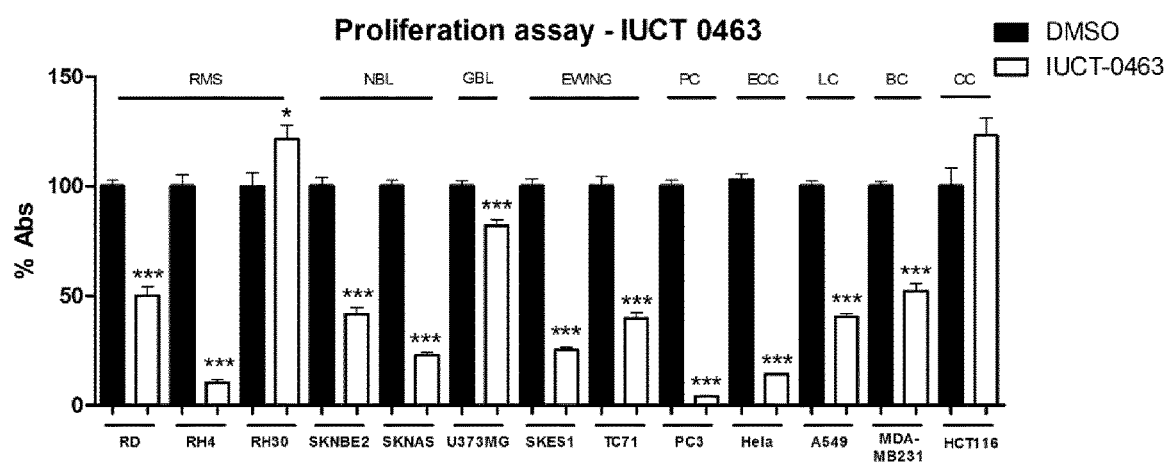
FIG. 5 represents the effects (in percentage with respect to the vehicle control DMSO) of the most active compound IUCT-0463 (10 microM) on cell growth of a panel of cancer cell lines after 5 day incubation (mean+/−SD). The cell lines analyzed are as follows: RD, RH4 and RH30 (rhabdomyosarcoma, RMS); SKNBE2 and SKNAS (neuroblastoma, NBL); U373MG (glioblastoma, GBL); SKES1 and TC71 (Ewing's sarcoma, EWING); PC3 (prostate cancer, PC); HeLa (epitheloid cervix carcinoma, ECC); A549 (lung cancer, LC); MDA-MB231 (breast cancer, BC) and HCT116 (colorectal cancer, CC). Statistical analysis was performed using ANOVA. As statistical differences were observed (p=0), the pairwise comparison against the vehicle control was made using the Tukey test. Notation: *=statistically-significant difference with a p-value<0.001, =p-value<0.01 and *=p-value<0.05.

With the compound showing a better cell growth reduction (IUCT-0463), additional tests were performed with the aim of studying the possible application of this family of compounds to other cancers. The procedure was carried out in a 96-well plate and cells were fixed for 30 minutes with 4% paraformaldehyde (PFA) at room temperature. After 3 washes with phosphate-buffered saline (PBS), cells were stained for 30 minutes at room temperature with Methyl violet (dilution 1/25 of a stock solution made with 1.5% w/v in PBS). After 5 washes, and the addition of acetic acid (15% in water), plates were read in a spectrophotometer at 590 nm. All conditions were tested in 8 independent wells and results expressed as a mean of all replicates The results showed high anti-proliferative activity in the majority of cell lines analysed (FIG. 5). The compound IUCT-0463 showed a remarkable reduction of cell proliferation in the majority of the cell lines analized.

In the light of the prior examples, results on the compounds of formula (I) strongly demonstrate a remarkable anti-oncogenic activity, with particularly good response for the compound N-(1-(3-fluoro-2'-methoxy-[1,1'-biphenyl]-4-yl)-2-oxopiperidin-3-yl)-5-(pyridin-2-yl)thiophene-2-sulfonamide, in all cases better than the reference compound Vismodegib. The anti-oncogenic activity was observed in two rhabdomyosarcoma cell lines as well as in a panel of cancer cell lines including a wide range of cancer types, being the growth of the majority of them severely affected by the treatment using compounds of formula (I).

Taken together, these results strongly suggest the family of compounds of formula (I) as a novel and potent new therapeutic agents against cancer, which may have the potential to improve current therapeutic protocols and, therefore, to improve survival and quality of life of cancer patients.

REFERENCES

Allen B L, et al. The Hedgehog-binding proteins Gas1 and Cdo cooperate to positively regulate Shh signaling during mouse development. Genes Dev. 2007; 21: 1244-1257.

Almazán-Moga A, et al. Hedgehog Pathway Inhibition Hampers Sphere and Holoclone Formation in Rhabdomyosarcoma. Stem Cells Int. 2017; 2017:7507380.

Almazán-Moga A, et al. Ligand-dependent Hedgehog pathway activation in Rhabdomyosarcoma: the oncogenic role of the ligands. Br J Cancer. 2017; 117(9):1314-1325.

Catenacci D V, et al. Randomized Phase Ib/II Study of Gemcitabine Plus Placebo or Vismodegib, a Hedgehog Pathway Inhibitor, in Patients with Metastatic Pancreatic Cancer. J. Clin. Oncol. 2015. 33(36):4284-92.

Gibert B, et al. Regulation by miR181 family of the dependence receptor CDON tumor suppressive activity in neuroblastoma. J Natl Cancer Inst. 2014; 13; 106(11).

Hayashi T, et al. Identification of transmembrane protein in prostate cancer by the *Escherichia coli* ampicillin secretion trap: expression of CDON is involved in tumor cell growth and invasion. Pathobiology. 2011; 78(5):277-84.

Leem Y E, et al. CDO, an Hh-Coreceptor, Mediates Lung Cancer Cell Proliferation and Tumorigenicity through Hedgehog Signaling. PLos One. 2014; 9(11):e111701.

Manzella G, et al. Interfering with Hedgehog Pathway: New Avenues for Targeted Therapy in Rhabdomyosarcoma. Curr Drug Targets 2015; 2016; 17(11):1228-34.

McMillan R, et al. Molecular pathways: the hedgehog signaling pathway in cancer. Clin. Cancer Res. 2012; 18: 4883-4888.

Mille F, et al. The Shh receptor Boc promotes progression of early medulloblastoma to advanced tumors. Dev Cell. 2014; 13; 31(1):34-47.

Okada A, et al. Boc is a receptor for sonic hedgehog in the guidance of commissural axons. Nature. 2006; 444: 369-373.

Roma J, et al. Notch, Wnt, and Hedgehog pathways in rhabdomyosarcoma: from single pathways to an integrated network. Sarcoma 2012; 2012:695603.

Teglund S, et al. Hedgehog beyond medulloblastoma and basal cell carcinoma. Biochim Biophys Acta. 2010; 1805: 181-208.

Tenzen T, et al. The cell surface membrane proteins Cdo and Boc are components and targets of the Hedgehog signaling pathway and feedback network in mice. Dev Cell. 2006; 10:647-656.

Giles W. Robinson et al. Vismodegib Exerts Targeted Efficacy Against Recurrent Sonic Hedgehog-Subgroup Medulloblastoma: Results from Phase II Pediatric Brain Tumor Consortium Studies PBTC-025B and PBTC-032, Journal of Clinical Oncology, 2015, 33 (24), 2646-2654.

The invention claimed is:

1. A compound selected from the group consisting of:
   4,5-Dichloro-N-(1-(3-fluoro-2'-methoxy-[1,1'-biphenyl]-4-yl)-2-oxopiperidin-3-yl)thiophene-2-sulfonamide;
   N-(1-(3-fluoro-2'-methoxy-[1,1'-biphenyl]-4-yl)-2-oxopiperidin-3-yl)-3,5-dimethylisoxazole-4-sulfonamide;
   N-(1-(3-fluoro-2'-methoxy-[1,1'-biphenyl]-4-yl)-2-oxopiperidin-3-yl)benzo[d][1,3] dioxole-5-sulfonamide;
   N-(1-(3-fluoro-2'-methoxy-[1,1'-biphenyl]-4-yl)-2-oxopiperidin-3-yl)-5-(pyridin-2-yl)thiophene-2-sulfonamide;
   N-(1-(3-fluoro-2'-methoxy-[1,1'-biphenyl]-4-yl)-2-oxopiperidin-3-yl)benzofuran-2-sulfonamide;
   4,5-Dichloro-N-(cyanomethyl)-N-(1-(3-fluoro-2'-methoxy-[1,1'-biphenyl]-4-yl)-2-oxopiperidin-3-yl)thiophene-2-sulfonamide;
   Ethyl N-(benzo[d][1,3]dioxol-5-ylsulfonyl)-N-(1-(3-fluoro-2'-methoxy-[1,1'-biphenyl]-4-yl)-2-oxopiperidin-3-yl)glycinate;
   N-(1-(3-fluoro-2'-methoxy-[1,1'-biphenyl]-4-yl)-2-oxopiperidin-3-yl)-N-(2-morpholino-2-oxoethyl)benzo[d][1,3]dioxole-5-sulfonamide;
   2-((4,5-dichloro-N-(1-(3-fluoro-2'-methoxy-[1,1'-biphenyl]-4-yl)-2-oxopiperidin-3-yl)thiophene)-2-sulfonamido)acetamide; and
   Ethyl N-(1-(3-fluoro-2'-methoxy-[1,1'-biphenyl]-4-yl)-2-oxopiperidin-3-yl)-N-((5-(pyridin-2-yl)thiophen-2-yl)sulfonyl)glycinate;
   or a salt thereof.

2. The compound according to claim 1, which is N-(1-(3-fluoro-2'-methoxy-[1,1'-biphenyl]-4-yl)-2-oxopiperidin-3-yl)-5-(pyridin-2-yl)thiophene-2-sulfonamide.

3. The compound according to claim 1, wherein the compound inhibits cell proliferation of a cancer cell, wherein the cancer is lung cancer, prostate cancer, colorectal cancer, breast cancer, cervical cancer, glioblastoma, neuroblastoma, rhabdomyosarcoma, or osteosarcoma.

4. The compound according to claim 1, wherein the compound inhibits cell proliferation of a cancer cell, wherein the cancer is epitheloid cervix carcinoma, basal cell carcinoma, melanoma, ovarian cancer, cervical cancer, pancreatic cancer, rhabdomyosarcoma, osteosarcoma, Ewing sarcoma, medulloblastoma, glioblastoma, astrocytoma, neuroblastoma, prostate cancer, lung cancer or breast cancer.

5. The compound according to claim 1, wherein the compound inhibits cell proliferation of a cancer cell, wherein the cancer is rhabdomyosarcoma, neuroblastoma, glioblastoma, Ewing's sarcoma, prostate cancer, epitheloid cervix carcinoma, lung cancer or breast cancer.

6. A combination comprising a compound according to claim 1 and compound selected from the group consisting of a chemotherapeutic agent; an antimetabolite; a spindle poison plant alkaloid; a cytotoxic/antitumour antibiotic; a topoisomerase inhibitor; an antibody; a photosensitizer; a kinase inhibitor; a pathway-specific inhibitor; an anti-hormonal agent; an aromatase inhibitor; an anti-androgen; a ribozyme; a vaccine; an anti-angiogenic agent; and an antiviral agent; or a combination thereof.

7. A pharmaceutical composition comprising a compound according to claim 1.

8. The pharmaceutical composition of claim 7, wherein the composition is formulated for administration by an oral, rectal, nasal, ocular, topical, vaginal, parenteral, transdermal, intraperitoneal, intrapulmonary or intranasal route.

9. A method of treating a cancer selected from the group consisting of lung cancer, prostate cancer, colorectal cancer, breast cancer, cervical cancer, glioblastoma, neuroblastoma, rhabdomyosarcoma, or osteosarcoma, comprising the step of administering to a subject in need thereof a therapeutically effective amount of a compound according to claim 1.

10. The method of claim 9, further comprising the step of administering a compound selected from the group consisting of a chemotherapeutic agent; an antimetabolite; a spindle poison plant alkaloid; a cytotoxic/antitumour antibiotic; a topoisomerase inhibitor; an antibody; a photosensitizer; a kinase inhibitor; a pathway-specific inhibitor; an anti-hormonal agent; an aromatase inhibitor; an anti-androgen; a ribozyme; a vaccine; an anti-angiogenic agent; and an antiviral agent; or a combination thereof.

11. The method of claim 9, wherein said compound is included in a pharmaceutical composition.

12. The method of claim 9, wherein said compound is administered by oral, rectal, nasal, ocular, topical, vaginal, parenteral, transdermal, intraperitoneal, intrapulmonary or intranasal route.

13. The method of claim 9, wherein said compound is administered in combination with surgical therapy, radiotherapy, immunotherapy, epigenetic therapy or a combination thereof.

14. A method of treating a cancer selected from the group consisting of epitheloid cervix carcinoma, basal cell carcinoma, melanoma, ovarian cancer, cervical cancer, pancreatic cancer, rhabdomyosarcoma, osteosarcoma, Ewing sarcoma, medulloblastoma, glioblastoma, astrocytoma, neuroblastoma, prostate cancer, lung cancer or breast cancer, comprising the step of administering to a subject in need thereof a therapeutically effective amount of a compound according to claim 1.

15. A method of treating a cancer selected from the group consisting of rhabdomyosarcoma, neuroblastoma, glioblastoma, Ewing's sarcoma, prostate cancer, epitheloid cervix carcinoma, lung cancer or breast cancer, comprising the step of administering to a subject in need thereof a therapeutically effective amount of a compound according to claim 1.

* * * * *